US012417827B2

(12) United States Patent
Prasad

(10) Patent No.: US 12,417,827 B2
(45) Date of Patent: Sep. 16, 2025

(54) TELECOMMUNICATION APPARATUS AND METHOD

(71) Applicant: SurgiPrice, Inc., Rockville, MD (US)

(72) Inventor: Sanjay Prasad, Rockville, MD (US)

(73) Assignee: SurgiPrice, Inc., Rockville, MD (US)

( * ) Notice: Subject to any disclaimer, the term of this patent is extended or adjusted under 35 U.S.C. 154(b) by 186 days.

(21) Appl. No.: 17/961,900

(22) Filed: Oct. 7, 2022

(65) Prior Publication Data
US 2023/0154579 A1 May 18, 2023

Related U.S. Application Data

(60) Provisional application No. 63/278,695, filed on Nov. 12, 2021.

(51) Int. Cl.
G16H 10/60 (2018.01)

(52) U.S. Cl.
CPC .................................. *G16H 10/60* (2018.01)

(58) Field of Classification Search
CPC ....................................................... G16H 10/60
See application file for complete search history.

(56) References Cited

U.S. PATENT DOCUMENTS

| 7,260,480 B1* | 8/2007 | Brown .................... G16H 50/80 703/11 |
| 9,129,054 B2* | 9/2015 | Nawana ................ A61B 5/4848 |
| 9,171,285 B2* | 10/2015 | Greene ................. G06Q 10/087 |
| 9,928,342 B1* | 3/2018 | LaBorde ................. G06N 3/048 |
| 10,014,076 B1* | 7/2018 | LaBorde ................. G16H 10/65 |
| 10,043,591 B1* | 8/2018 | LaBorde ................. G06N 3/08 |
| 10,186,329 B1* | 1/2019 | LaBorde ................. G06N 3/084 |
| 10,192,636 B1* | 1/2019 | LaBorde ................. G06N 3/04 |
| 10,319,476 B1* | 6/2019 | LaBorde ................. G06N 3/08 |
| 10,388,410 B1* | 8/2019 | LaBorde ................. G16H 50/70 |
| 10,460,837 B1* | 10/2019 | LaBorde ................. G06N 3/048 |

(Continued)

FOREIGN PATENT DOCUMENTS

| EP | 2000934 A1 * | 12/2008 | .......... G06F 19/324 |
| WO | WO-2006125145 A2 * | 11/2006 | .......... G06F 19/321 |
| WO | WO-2008149300 A1 * | 12/2008 | .......... G06F 19/324 |

OTHER PUBLICATIONS

Demiris, Elsevier, 2019, pp. 311-330.*

(Continued)

Primary Examiner — Michael I Ezewoko
(74) Attorney, Agent, or Firm — Buchanan Ingersoll & Rooney PC

(57) ABSTRACT

Telecommunication systems and telecommunication devices can be configured for collecting and corroborating medical data obtained from at least one electronic medical record database via at least one network connection (e.g. the internet, an intranet, a local area network, a wide area network, etc.). Embodiments can be configured to corroborate data obtained to confirm user input that has been entered by a user is corroborated by other medical record documentation. Embodiments can help evaluate self-reported data provided by a care provider user to provide an objective evaluation of that data to minimize misrepresentative data or inaccurate data being utilized in conjunction with one or more telecommunication services that can be hosted by the system or device.

18 Claims, 7 Drawing Sheets

(56) References Cited

U.S. PATENT DOCUMENTS

| | | | |
|---|---|---|---|
| 10,482,377 B1 * | 11/2019 | LaBorde | G06N 3/048 |
| 10,628,739 B1 * | 4/2020 | LaBorde | G06N 3/088 |
| 10,777,306 B1 * | 9/2020 | LaBorde | G06Q 10/08 |
| 10,783,991 B1 * | 9/2020 | LaBorde | G06Q 50/22 |
| 11,238,962 B1 * | 2/2022 | LaBorde | G06N 3/088 |
| 11,355,223 B1 * | 6/2022 | LaBorde | G06N 3/048 |
| 11,593,606 B1 * | 2/2023 | LaBorde | G06N 3/08 |
| 11,705,242 B2 * | 7/2023 | Pfeiffer | G16H 40/20 |
| | | | 705/2 |
| 11,735,299 B1 * | 8/2023 | LaBorde | G16H 10/65 |
| | | | 340/10.1 |
| 2003/0191668 A1 | 10/2003 | Oka et al. | |
| 2005/0187794 A1 | 8/2005 | Kimak | |
| 2006/0149593 A1 | 7/2006 | Wager | |
| 2006/0161456 A1 | 7/2006 | Baker et al. | |
| 2007/0027720 A1 | 2/2007 | Hasan et al. | |
| 2007/0156455 A1 | 7/2007 | Tarino et al. | |
| 2008/0177576 A1 | 7/2008 | Jennings et al. | |
| 2012/0310661 A1 * | 12/2012 | Greene | G06Q 10/087 |
| | | | 705/2 |
| 2013/0246084 A1 | 9/2013 | Parmanto et al. | |
| 2014/0240444 A1 | 8/2014 | Szymczyk et al. | |
| 2015/0261917 A1 | 9/2015 | Smith | |
| 2015/0287082 A1 | 10/2015 | Agarwal | |
| 2015/0294079 A1 | 10/2015 | Bergougnan | |
| 2017/0011192 A1 | 1/2017 | Arshad et al. | |
| 2017/0249435 A1 | 8/2017 | Lancelot | |
| 2017/0323485 A1 | 11/2017 | Samec et al. | |
| 2018/0226158 A1 | 8/2018 | Fish et al. | |
| 2018/0360295 A1 | 12/2018 | Boucher et al. | |
| 2019/0392931 A1 | 12/2019 | Abousy et al. | |
| 2020/0311781 A1 * | 10/2020 | Kalmat | G06Q 10/04 |
| 2021/0240852 A1 | 8/2021 | Shelton et al. | |
| 2021/0304860 A1 | 9/2021 | Hart et al. | |
| 2021/0350915 A1 * | 11/2021 | Letinic | G06F 40/30 |
| 2024/0233895 A1 * | 7/2024 | LaBorde | G16H 40/63 |

OTHER PUBLICATIONS

International Search Report for Application No. PCT/US2022/048514 dated Mar. 9, 2023.

Written Opinion of the International Searching Authority for Application No. PCT/US2022/048514 dated Mar. 9, 2023.

* cited by examiner

| | | | Colonoscopy | | | |
|---|---|---|---|---|---|---|
| Best Practice Weighting | | | 20% | 90% | 0.001 | |
| Surgeon | Volume | ADR | Cecal Intubation Rate | Perforation Rate | | Star Rating |
| 1 | 20 | 5% | 80% | 0.05 | ☆ | 1 |
| 2 | 40 | 5.40% | 80% | 0.049 | ☆ | 1 |
| 3 | 60 | 6% | 80% | 0.048 | ☆ | 1 |
| 4 | 80 | 6.20% | 81% | 0.047 | ☆ | 1 |
| 5 | 100 | 7% | 81% | 0.046 | ☆ | 1 |
| 6 | 120 | 7.00% | 81% | 0.045 | ☆ | 1 |
| 7 | 140 | 7% | 81% | 0.044 | ☆ | 1 |
| 8 | 160 | 7.80% | 81% | 0.043 | ☆ | 1 |
| 9 | 180 | 8% | 82% | 0.042 | ☆ | 1 |
| 10 | 200 | 8.60% | 82% | 0.041 | | 2 |
| 11 | 220 | 9% | 82% | 0.04 | | 2 |
| 12 | 240 | 9.40% | 82% | 0.039 | | 2 |
| 13 | 260 | 10% | 82% | 0.038 | | 2 |
| 14 | 280 | 10.20% | 83% | 0.037 | | 2 |
| 15 | 300 | 11% | 83% | 0.036 | | 2 |
| 16 | 320 | 11.00% | 83% | 0.035 | | 2 |
| 17 | 340 | 11% | 83% | 0.034 | | 2 |
| 18 | 360 | 11.80% | 83% | 0.033 | | 2 |
| 19 | 380 | 12% | 84% | 0.032 | | 2 |
| 20 | 400 | 12.60% | 84% | 0.031 | | 3 |
| 21 | 420 | 13% | 84% | 0.03 | | 3 |

FIG. 8

TELECOMMUNICATION APPARATUS AND METHOD

CROSS-REFERENCE TO RELATED APPLICATIONS

The present application claims priority to U.S. Provisional Patent Application No. 63/278,695, filed on Nov. 12, 2021.

FIELD

The present innovation relates to telecommunication systems, devices, and methods for use in providing at least one telecommunication service that can be hosted by at least one telecommunication device via at least one communication network.

BACKGROUND

Electronic medical records are often stored by one or more health care provider systems. Such records can be used in conjunction with the providing of medical care to a patient. Examples of telehealth systems and other medical treatment processes that may utilize such records can be found in U.S. Pat. App. Pub. Nos. 2021/0240852, 2021/0304860, 2020/0311781, 2019/0392931, 2018/0360295, 2018/0226158, 2017/0323485, 2017/0249435, 2017/0011192, 2015/0294079, 2015/0261917, 2014/0240444, 2013/0246084, 2008/0177576, 2007/0027720, 2006/0161456, 2005/0187794, and 2003/0191668.

Electronic systems also exist for providing a personalized medical care provider concierge service. The SurgiQuality platform is one example of this type of service. This platform can help a user gather pertinent medical records and imaging for upload, send the records and imaging to various surgeons to receive their input on the records, their past experience with a patient's condition, and a price for a proposed medical procedure for presenting to a user via a user's smart phone, laptop or tablet device. The user can then use that information to pick a particular surgeon and also utilize the service to contact the different surgeons who responded to the user's initial query with the user's uploaded medical records and imaging.

SUMMARY

It has been determined that care provider promotional materials that can be provided to users of a telecommunication system can be inaccurate. This information can be based on input obtained from the care provider and be misleading by overstating the expertise or experience of the care provider, for example. It has been determined that a new methodology for evaluating care provider data to corroborate its accuracy is needed for selecting data to be displayed to users to allow users to make more informed, accurate decisions when using a telecommunication service to facilitate their selection of a care provider to provide a service to the user or a user's friend or family member.

Systems, devices, and methods can be provided to corroborate medical provider data that may be input into a system in conjunction with promotion of the medical provider's services. Embodiments of the system, device, and method can help avoid a situation where a medical provider's input data misrepresents the level of expertise, skill, or experience of the provider. This can help improve communications for obtaining health care services, and help avoid situations where a care provider is selected for a service without a patient having a complete understanding of the care provider's level of skill or applicable experience. The improved communications provided by embodiments of the apparatus and method can help reduce incidents of malpractice, and help lower insurance premiums for care providers and patients. Objective processes for analyzing and corroboration of the data can be utilized to help avoid inaccurate understandings of data that can be displayed to a user in conjunction with at least one telecommunication service provided by a device hosting a telecommunication service accessible via at least one network (e.g. via an application programming interface (API) a device may have with at least one server via at least one communication network).

Embodiments of the device can be machines that include at least one processor communicatively connected to at least one non-tangible computer readable medium (e.g. at least one non-transitory memory, at least one solid state drive, flash memory, or hard drive, etc.) and at least one network interface (e.g. local area wireless interface such as a Wi-Fi transceiver, a near field communication interface such as a Bluetooth transceiver, a local area network interface such as an Ethernet interface, a cellular network transceiver, interfaces for combinations thereof etc.). Each device can also include input devices, output devices, and/or input/output devices such as touch screens, displays, speakers, microphones, cameras, headphones, head sets, pointer devices, keyboards, stylus devices, buttons or printers. Such input and/or output devices can be communicatively connected to the processor and/or non-tangible computer readable medium via a wireless connection (e.g. Bluetooth) or via a wired connection (e.g. universal serial bus (USB) connection).

Embodiments of a telecommunication system can include at least one telecommunication device. In some embodiments the telecommunication system can include a server that hosts at least one telecommunication service that can be provided to one or more terminal devices (e.g. smart phones, tablets, laptop computers, personal computers, etc.) via at least one network (e.g. the internet, etc.). The server can be a machine that has at least one processor communicatively connected to at least one non-tangible computer readable medium (e.g. at least one non-transitory memory, at least one solid state drive, flash memory, or hard drive, etc.) and at least one network interface (e.g. local area wireless interface such as a Wi-Fi transceiver, a near field communication interface such as a Bluetooth transceiver, a local area network interface such as an Ethernet interface, a cellular network transceiver, combinations thereof, etc.).

In some embodiments, the server of other telecommunication device that can host at least one telecommunication service can be configured to retrieve data from one or more electronic health record (EHR) systems that maintain one or more electronic medical record (EMR) databases via at least one network connection to obtain the EMR records concerning services provided by one or more health care providers and/or to query the EMR data to retrieve query results to obtain portions of data retained within the EMR records. The retrieved data can be stored in the server's memory or other memory accessible to the server, and subsequently analyzed to compare the care provider data input to the server via the care provider with medical record data to objectively determine the accuracy of the care provider's input data. That analyzed data can subsequently be further processed to evaluate the quality of the care provider's services as compared to other care providers' data stored in memory accessible to the server for rating the care providers services relative to the other care providers. Such evaluations can be performed for different services that the care provider can offer to a user. The evaluation results can be communicated to a user device via a telecommunication connection so a graphical user interface (GUI) is generatable at a display of a user device to display the care providers' evaluated quality ratings determined by the server and/or data input by the service care providers that has been corroborated as accurate via the evaluation of retrieved data from the EMRs. In some embodiments, the communication for generation of the GUI at a user terminal device's display (e.g. display of a patient device) can be provided via an API interface, for example.

In some embodiments, a telecommunication apparatus can include a host device having a processor connectable to a non-transitory computer readable medium. The host device can be configured to communicate with at least one electronic health record (EHR) device, at least one practice management element, at least one care provider device, and at least one patient device via at least one network. The host device can be configured to query electronic medical records stored at the EHR device(s) and/or practice management element(s) and compare self-reported data associated with a care provider received via the at least one care provider device with medical records associated with the care provider accessible via the EHR device and/or the at least one practice management element.

The host device can be configured to evaluate at least one success measure based on a pre-selected success criteria and/or at least one complication measure based on pre-selected complication criteria from comparing the self-reported data with data from the queried medical records to corroborate the self-reported data. The host device can also be configured to filter the corroborated self-reported data based on filtering input received via the at least one patient device to display care provider data responsive to the filtering input. The filtered corroborated self-reported data can be prioritizable based on a pre-selected prioritization weighing function so that care provider data is displayable via a graphical user interface (GUI) displayed at a patient device in accordance with a ranking defined by the weighing function that is determined by the host device.

In some embodiments, the pre-selected success criteria can include a generated quality metric for a critical view of safety (CVS) criteria. The quality metric for CVS can be determinable by the host device via a recognition of anatomical structure outlines from image data and/or video data received from the at least one patient device associated with a care provider.

Some embodiments of the telecommunication apparatus can include more than just the host device. For instance, embodiments can include at least one patient device, at least one care provider device, at least one practice management element, at least one EHR device, and/or at least one network.

A method of telecommunication is also provided. The method can include a host device communicating with at least one electronic health record (EHR) device and/or at least one practice management element to query electronic medical records stored at the EHR device and/or at least one practice management element. The host device can compare self-reported data associated with a care provider received via at least one care provider device with medical records associated with the care provider accessible via the communicating with the EHR device and/or the at least one practice management element.

Embodiments of the method can also include other steps. For instance, the host device can evaluate at least one success measure based on a pre-selected success criteria and/or at least one complication measure based on pre-selected complication criteria from comparing the self-reported data with data from the queried medical records to corroborate the self-reported data. The host device can also filter the corroborated self-reported data based on filtering input received from at least one patient device to display care provider data responsive to the filtering input. The host device can also prioritize the filtered corroborated self-reported data based on a pre-selected prioritization weighing function so that care provider data is displayable via a GUI displayed at the at least one patient device in accordance with a ranking defined by the weighing function that is determined by the host device.

As noted above, embodiments can be configured so that the pre-selected success criteria includes a generated quality metric for a critical view of safety (CVS) criteria. The quality metric for CVS can be determinable by the host device via a recognition of anatomical structure outlines from image data and/or video data received from the at least one patient device associated with a care provider.

The at least one success measure can include success rate and the at least one complication measure can include a complication rate.

A non-transitory computer readable medium having an application stored thereon is also provided. The application stored in the medium can define a method that is performed by a telecommunication device that runs the application. The method can include an embodiment of a method discussed herein. For instance, the method can include the telecommunication device communicating with at least one electronic health record (EHR) device and/or at least one practice management element to query electronic medical records stored at the EHR device and/or at least one practice management element. The defined method can also include the telecommunication device comparing self-reported data associated with a care provider received via at least one care provider device with medical records associated with the care provider accessible via the communicating with the EHR device and/or the at least one practice management element.

The telecommunication device can evaluate at least one success measure based on a pre-selected success criteria and/or at least one complication measure based on pre-selected complication criteria from comparing the self-reported data with data from the queried medical records to corroborate the self-reported data. The telecommunication device can also perform filtering of the corroborated self-reported data based on filtering input received from at least one patient device to display care provider data responsive to the filtering input. Also, the telecommunication device can prioritize the filtered corroborated self-reported data based on a pre-selected prioritization weighing function so that care provider data is displayable via a GUI displayed at the at least one patient device in accordance with a ranking defined by the weighing function that is determined by the host device.

As discussed above, an example of the pre-selected success criteria can include a generated quality metric for a critical view of safety (CVS) criteria. The telecommunication device can determine a quality metric for CVS via a recognition of anatomical structure outlines from image data and/or video data received from the at least one patient device associated with a care provider.

Other details, objects, and advantages of the telecommunications apparatus, system, device, non-transitory computer readable medium, and method will become apparent as the following description of certain exemplary embodiments thereof proceeds.

BRIEF DESCRIPTION OF THE DRAWINGS

Exemplary embodiments of the telecommunications apparatus, system, device, non-transitory computer readable medium, and method and embodiments thereof will be described below in further detail in connection with the drawings. It should be understood that like reference characters used in the drawings may identify like components.

FIG. 8 is an exemplary embodiment of a GUI display illustrating an exemplary display of filtered care provider data based on filtering input received from a patient device in the first exemplary embodiment of the telecommunication apparatus.

DETAILED DESCRIPTION

Figure 1:
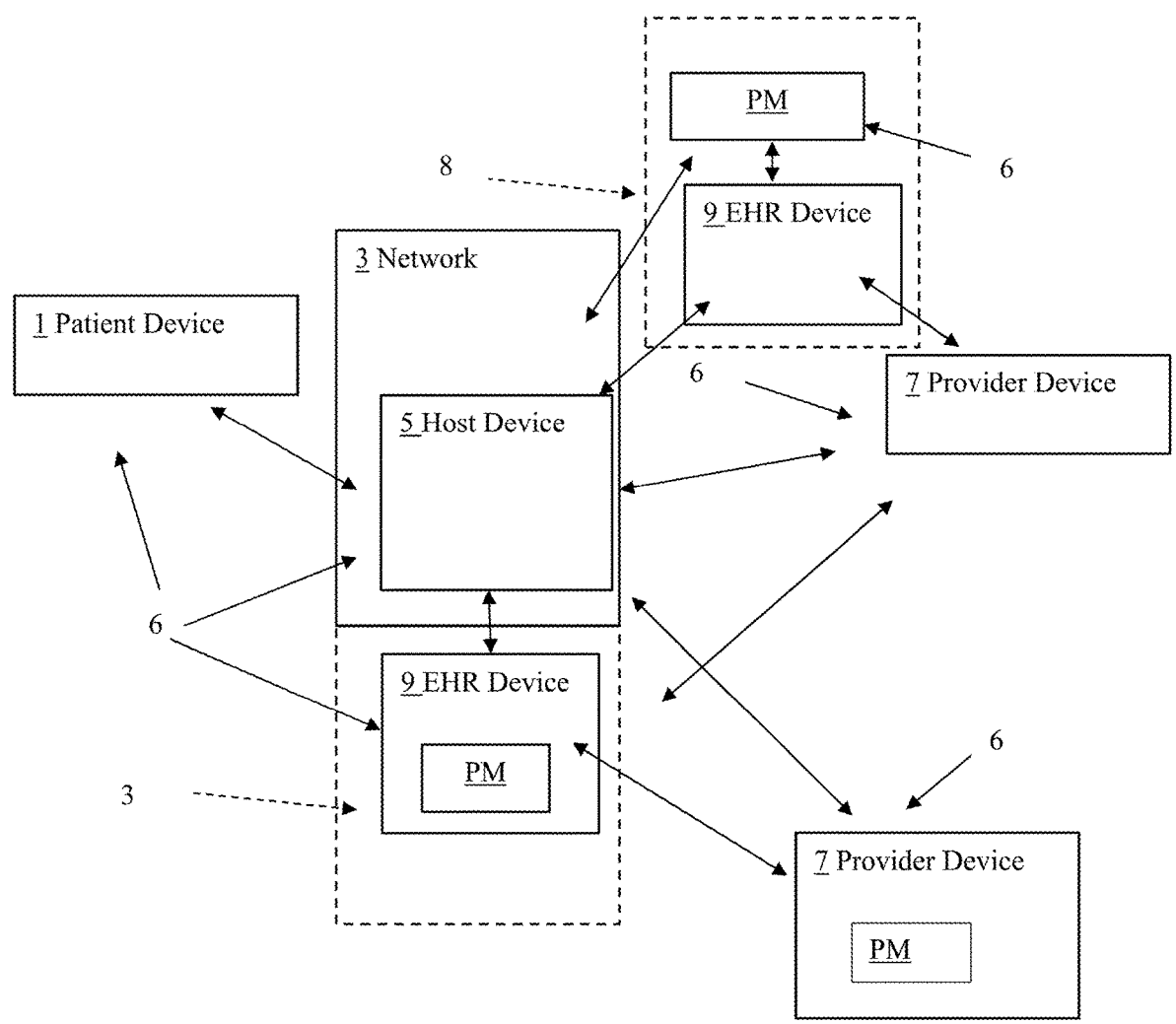
FIG. 1 is a block diagram of a first exemplary embodiment of a telecommunication apparatus.
Figure 2:
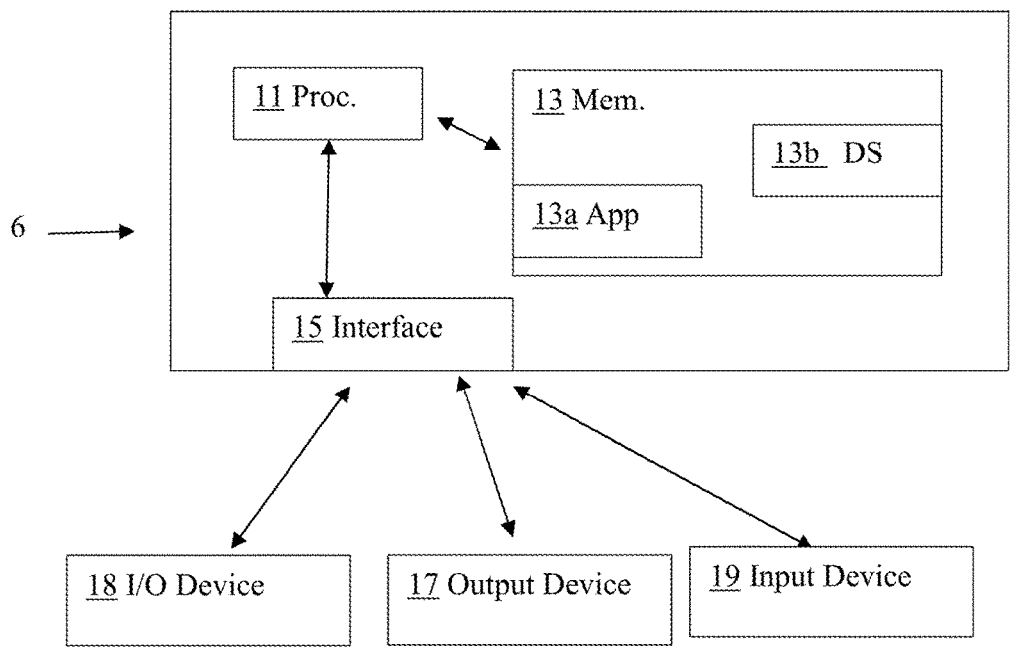
FIG. 2 is a block diagram of an exemplary telecommunication device that can be utilized in the first exemplary embodiment of the telecommunication apparatus.
Figure 3:
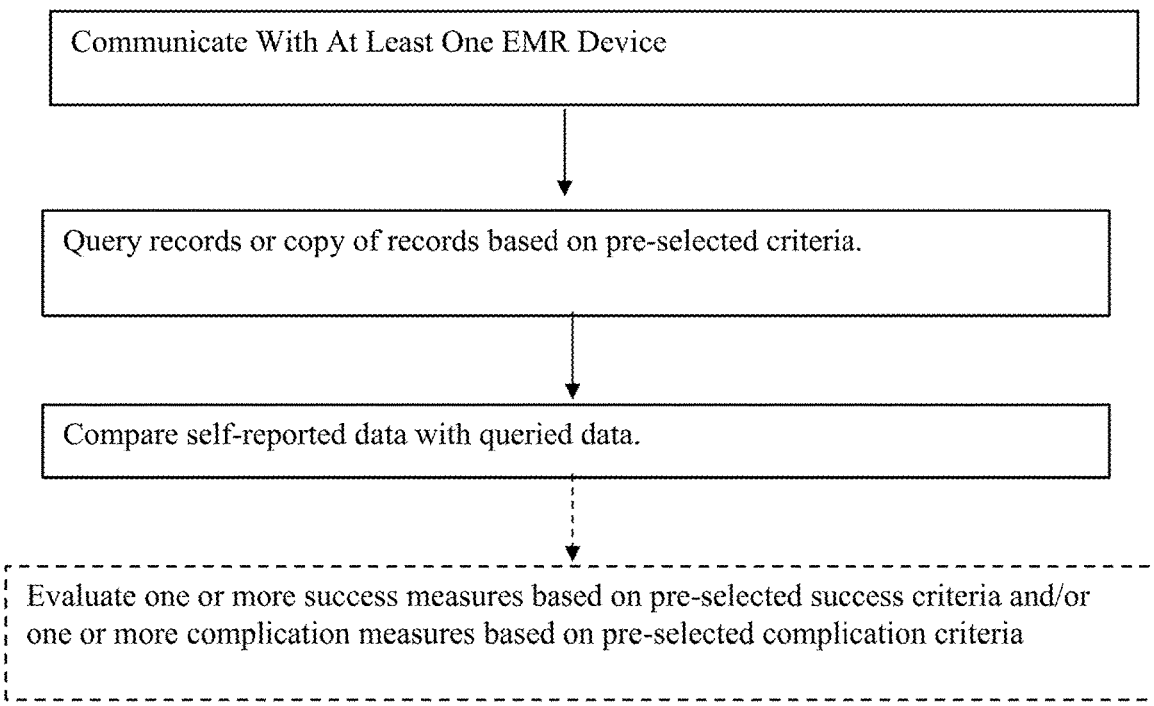
FIG. 3 is a flow chart illustrating an exemplary process for data corroboration that can be utilized in the first exemplary embodiment of the telecommunication apparatus. The process shown in FIG. 3 via broken line also illustrates a first exemplary process for data analysis of the corroborated data to determine one or more success measures and/or one or more complication measures that can be utilized in the first exemplary embodiment of the telecommunication apparatus.
Figure 4:
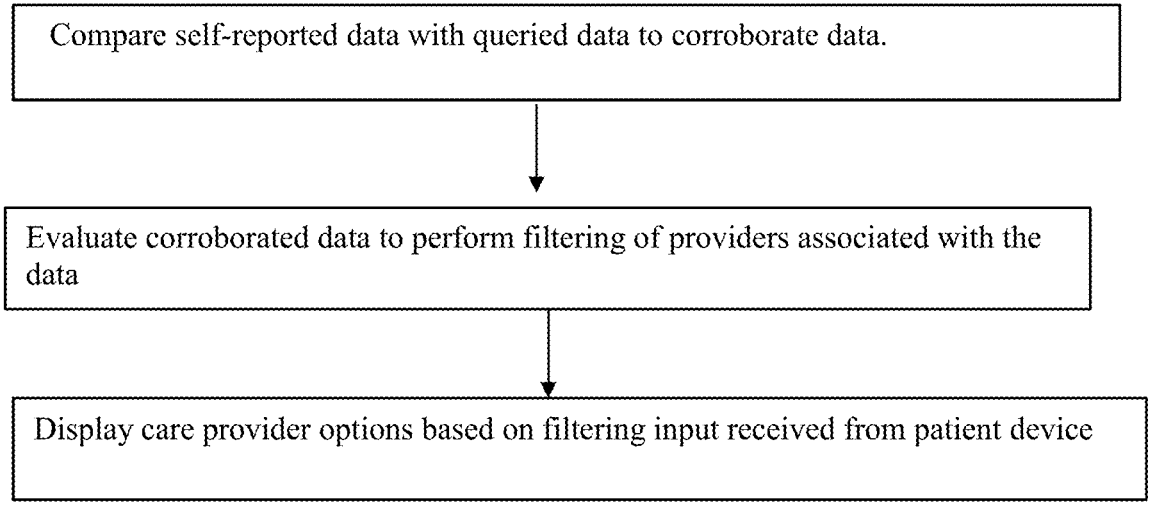
FIG. 4 is a flow chart illustrating an exemplary process for analyzing corroborated data that can be utilized for providing a filtered display in a GUI of a patient device in the first exemplary embodiment of the telecommunication apparatus.
Figure 5:
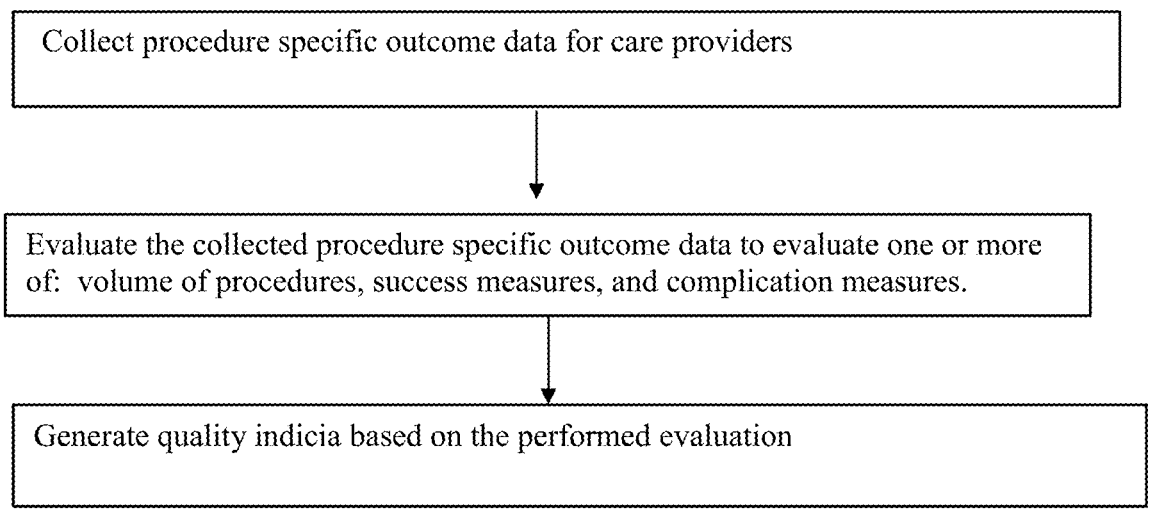
FIG. 5 is a flow chart illustrating an exemplary process for generating quality indicia for display in a GUI of a patient device 1 in the first exemplary embodiment of the telecommunication apparatus.

Referring to FIGS. 1-2, a communication apparatus can include multiple computer devices 6 that can include a patient device 1 that can communicatively connect to at least one host device 5 via at least one network 3 (e.g. the internet, a local area network, a wide area network, an intranet, a combination of such networks, etc.). The communication apparatus can also include a healthcare provider system 8 that includes an electronic health record (EHR) device 9 and/or one or more EHR devices 9 that can be connectable via the network 3. As indicated in broken line in FIG. 1, in some embodiments, the host device 5 can be within the same network 3 that includes at least one EHR device 9. In other embodiments, the host device 5 can be in a separate network and can be communicatively connectable to at least one EHR device 9.

The host device 5 be a device that is remote from one or more healthcare provider systems 8 and can be communicatively connectable to at least one EHR device 9 of at least one healthcare provider system 8 via at least one network 3 as shown in FIG. 1. The host device 5 can be within the network 3 as shown in FIG. 1 or can be communicatively connectable to the network 3 for a communication connection with the EHR devices 9, one or more care provider devices 7, and one or more patient devices 1.

Examples of EHR devices 9 can include electronic medical record management system devices. Examples of EHR devices 9 that can be utilized can include EHR devices that are operated or controlled by different health care entities, such as, for example, Epic, Praxis EMR, Cerner, GE Healthcare, Meditech, eClinicalWorks, Nextgen, Allscripts, Practice Fusion, Greenway Health, as well as other entities' electronic medical record hosting EHR devices 9. Other examples of EHR devices 9 can include one or more registries that are controlled or hosted by the American College of Surgeons (ACS), College of Physicians and Surgeons, American Academy of Ophthalmology, American College of Mohs Surgery, or other care provider association, other care provider college, other care provider academy, or other type of care provider entity.

An EHR device 9 can include a practice management element PM. The practice management element PM can be practice management software run on the EHR device 9, for example. In other implementations, the practice management element PM can be a separate computer device 6 that can be communicatively connected to the EHR device 9 and/or the host device 5 or can be an element of another device (e.g. be practice management software that can be run on the care provider device 7 or communicatively connectable to the care provider device 7).

As can be appreciated from FIG. 1, in some implementations an EHR device 9 can include the practice management element PM. In other implementations, the EHR device 9 can be communicatively connected to the practice management element PM, which can be a separate computer device 6. In such implementations, the practice management element PM can be communicatively connected to the host device 5 via an internet connection and/or via the EHR device 9.

Care provider devices 7 can be communicatively connectable to a patient device 1 via the host device 5 as well as via other network connection mechanisms that may facilitate such a communication connection. Care provider devices 7 can also be communicatively connectable to one or more EHR devices 9 and/or one or more patient devices 1. The host device 5 can facilitate communications between a patient device 1 and one or more care provider devices 7. Each patient device 1 and each care provider device 7 can be a type of communication terminal such as, for example, a smart phone, a tablet, a laptop computer, or a desktop personal computer (PC).

As noted above, the care provider device 7 can also include a practice management element PM. The practice management element PM can be practice management software run on the care provider device 7, for example. In other implementations, the practice management element PM can be a separate computer device 6 that can be communicatively connected to the care provider device 7 and/or the host device 5 or can be an element of another device (e.g. be practice management software that can be run on the EHR device 9).

The practice management element PM can, in some cases, include data to be queried by the host device that the EHR device 9 may not have. For example, the practice management element PM can include Current Procedural Terminology (CPT) codes for procedures and surgeries that can be queried and/or obtained by the host device 5 that may not be available from the EHR device 9. The CPT codes can be a pre-defined set of codes that are used to indicate different types of medical procedures and/or treatments.

The EHR device 9 can also include CPT codes in the records stored by that device. In some instances, the CPT codes the EHR device 9 has may differ from the CPT codes the practice management element PM may have. For instance, an EHR device 9 can include CPT codes for office visits or other types of work while the practice management element may have CPT codes for procedures and surgeries that may be performed. The host device 5 can be configured to communicate with the EHR device 9 and/or the practice management element PM to query one or both elements to obtain the CPT codes associated with work history for a particular care provider or set of care providers.

The EHR device can include records that include International Classification of Diseases (ICD) codes. The ICD odes can be a pre-defined set of codes that are used to indicate different types of medical conditions (e.g. diseases, symptoms, abnormal findings, or other elements of a patient's diagnosis). The practice management element PM can also include records that have ICD codes. The host device 5 can be configured to communicate with the EHR device 9 and/or the practice management element PM to query one or both elements to obtain such ICD codes associated with work history for a particular care provider or set of care providers.

Embodiments of the apparatus can also include other network nodes that can facilitate communications between the devices, such as, for example, routers, access points, gateways, base stations, border control devices, or other node devices.

As may be appreciated from FIG. 2, each of the computer devices 6 can be configured as a communication device (e.g. a server, a communication terminal such as a laptop computer, smart phone, tablet, desktop computer, a document management server or database server, etc.) For example, the EHR device 9 can be a server or computer system configured to store health records for a number of patients, the host device 5 can be a server or other device that can host communication services between multiple communication terminals such as a patient device 1 and at least one care provider device 7, and the patient device 1 and care provider device 7 can each be a communication terminal, such as, for example, a smart phone, table, laptop computer, or personal computer.

As another example, the practice management element PM, when implemented as a separate computer device 6 instead of being an element of an EHR device 9 or care provider device 7, can be a server, work station, computer or computer system that has health records stored within its non-transitory computer readable medium that stores records for patients and/or care providers about their prior work (e.g. procedures performed for different patients having different conditions, etc.).

Each computer device 6 can include a processor (Proc.) 11 shown in FIG. 2. The processor can be a hardware processor that can be a core processor, microprocessor, central processing unit, array of interconnected processors, or other type of processor. The processor can be connected to non-transitory memory (Mem.) 13 and at least one interface 15 that can facilitate communication connections with other devices or networks. The one or more interfaces 15 can include a network connection interface, a cellular network connection interface, a wireless network connection interface, and at least one near field connection interface (e.g. a Bluetooth connection interface, etc.) The memory 13 can be flash memory, a hard drive, a solid state drive, or other type of non-transitory computer readable medium. The memory 13 can store at least one application ("App"), such as at least one App 13a, and can also store one or more other data stores 13b, such as a data store DS. One or more input/output (I/O) devices 18, output devices 17, and/or input devices 19 can be communicatively connected to the processor 11. I/O deices 18 can include a touchscreen for example. The output devices 17 can include a display, a monitor, a printer, and/or a speaker. The input devices 19 can include a microphone, a camera, a keyboard, a pointer device (e.g. a mouse or a stylus), a keypad, buttons, at least one motion sensor, or other type of input device 19. The input devices, I/O devices, and output devices can be connected to the processor 11 via a wireless connection (e.g. a Bluetooth connection) or a wired connection (e.g. a universal serial bus ("USB") connection, etc.). A user can manipulate the one or more input devices 19 and/or I/O devices 18 to provide input to the computer device 6.

The computer device 6 can also generate output, such as a graphical user interface (GUI) display, audible output, or other type of output (e.g. printout via a printer, etc.). The generated output can be based on running at least one application, receipt of data from one or more other devices (e.g. communication with a host device via an API interface provided via at least one network connection, etc.), and/or receipt of input from a user via an input device 19 and/or I/O device 18.

The host device 5 can be configured to host a communication service to provide one or more telecommunication services to patient devices 1 and care provider devices 7 to facilitate the connection between users of patient devices 1 and users of care provider devices 7 to allow for communications between these devices to facilitate the selection of a care provider for at least one health service to be rendered to a user of the patient device. The communications can be supported to facilitate users' review of information and promotional materials from care providers associated with the care provider devices 7 and also facilitate the care providers associated with the care provider devices 7 promoting their services, learning of potential new health care service opportunities, and facilitating the hiring of care provider to provide health care services for a user via communications exchanged between users and care providers that can be supported by host device 5 and/or be facilitated via the host device 5. In conjunction with such support services hosted by host device 5, the host device 5 can be configured to engage in various communications and computer processing activities to help facilitate improved communications to improve the telecommunications processing hosted by the host device and improve the user experiences at the care provider devices 7 and patient devices 1 via improved GUI functionality, improved communication techniques, and improved displays of information to facilitate connections between users having a particular health care services need and qualified care providers associated with care provider devices 7. In some embodiments, the apparatus, host device 5, patient device 1, and/or care provider device 7 can be configured to utilize or participate in different methods and processes. Exemplary processes that these devices can be utilized in are illustrated in FIGS. 3-7 to provide such improvements, for example.

Referring to FIGS. 3-7, the host device 5 can be configured to receive input data from one or more care provider devices 7 that provide care provider self-reported data to the host device 5. The self-reported data can include, for example, information indicating specialist services the care provider offers. This information can include at least one code or other data that is associated with a pre-selected number of different specialties defined at the host device 5. The information that is provided via the care provider device(s) 7 can also include other information related to each identified specialty, such as a number of patients treated within a pre-selected time period for the specialty service, number of care providers (e.g. surgeons, doctors, dentists, nurse practitioners, etc.) and an identification of the care provider personnel that is qualified for providing the specialty service and is associated with the identified number of patients treated within the pre-selected time period for the specialty service. Examples of pre-selected specialty services can include, for example:

a. Rheumatology—Areas of Interest
 i. rheumatoid arthritis,
 ii. osteoarthritis,
 iii. crystalline diseases (e.g. such as gout),
 iv. spondyloarthropathies,
 v. vasculitis (e.g. such as giant cell arteritis or polyarteritis nodosa),
 vi. polymyalgia rheumatica,
 vii. systemic lupus erythematosus,
 viii. inflammatory muscle diseases (e.g such as polymyositis and dermatomyositis),
 ix. systemic sclerosis (e.g. scleroderma),
 x. Sjögren disease,
 xi. polychondritis,
 xii. osteoporosis,
 xiii. fibromyalgia, and
 xiv. common musculoskeletal and sports injuries.

Other examples of pre-selected specialty services can include dental related specialties, such as, for example:
 a. orthodontics and dentofacial orthopedics;
 b. pediatric dentistry
 c. periodontics
 d. prosthodontics;
 e. oral and maxillofacial surgery;
 f. oral and maxillofacial pathology;
 g. endodontics;
 h. public health dentistry
 i. oral and maxillofacial radiology.

Yet other examples of specialty services can include:
 a. surgery;
 b. internal medicine;
 c. radiology;
 d. anesthesiology;
 e. ophthalmology;
 f. dermatology;
 g. cardiology;
 h. oncology;
 i. neurology;
 j. emergency and critical care; and
 k. sports medicine and rehabilitation It should be appreciated that the specialties can include human health care specialties as well as veterinarian specialties for animal and/or pet health care. The particular specialties can be pre-defined to include a pre-selected number of specialty categories. The defined categories can be defined in some embodiments so that synonyms for a particular specialty are grouped into a single specialty type classification.

The host device 5 can maintain the received specialty data and other care provider data received from each care provider device 7 in a data store 13b that is accessible to the processor 11 of the host device. The data can be received via at least one network connection facilitated by at least one interface 15 of the host device 5. The host device's processor 11 can run at least one application 13a that defines a method that is performed by the host device for receipt of the care provider data, storage of that data, and subsequent processing and/or analysis of that data. The application can call on various programs or other pre-defined program routines to facilitate the running of the application.

The self-reported care provider data received from the care provider devices 7 can be corroborated by the host device 5 running one or more pre-defined data corroboration processes via its processor 11. Examples of such processes can be appreciated from FIGS. 3-7.

For example, the host device 5 can communicate with at least one EHR device 9 to obtain copies of medical records associated with the care provider's specialty services identified via the specialty data previously provided by the care provider device 7. These records can be stored in at least one data store 13b in memory 13 and subsequently queried. Alternatively, the host device 5 can communicate with the EHR device to query the medical records maintained by and/or stored by the EHR device 9 without obtaining copies of the actual medical records for storage at the host device or in memory accessible to the host device 5 for subsequent querying and analysis or evaluation.

The host device 5 can also communicate with at least one practice management element PM to obtain copies of medical records associated with the care provider's specialty services identified via the specialty data previously provided by the care provider device 7. These records can be stored in at least one data store 13b in memory 13 and subsequently queried. Alternatively, the host device 5 can communicate with the practice management element PM to query the medical records and/or billing records maintained by and/or stored by the practice management element PM without obtaining copies of the actual records for storage at the host device 5 or in memory accessible to the host device 5 for subsequent querying and analysis or evaluation.

Examples of queries that can be utilized by the host device 5 can include querying Current Procedural Terminology (CPT) codes and/or international classification of disease codes (e.g. ICD-10 codes, which can also be referred to as ICD-10-CM codes, ICD-9 codes which can also be referred to as ICD-9-CM codes, etc.). The codes that can be queried can be three digit, four digit or five digit codes in some embodiments and the querying can account for the digits of these codes and a pre-selected alphanumeric order for such codes.

The querying of the medical record data obtained or accessible via the one or more EHR devices 9 and/or one or more practice management elements PM that can be performed by the host device 5 can include a query for success and complication related data in the operative notes, postoperative notes of a medical record and/or a query for related postop surgeries related to the original condition treated in the record. The querying that is performed can also be structured to identify an abrupt change in the treating physician to identify a possible complication measure or quality issue. The querying that is performed can be structured to follow that episode of care for a particular condition associated with a record so all records related to a particular patient's condition is evaluated in the querying for each set of records associated with a care providers work in a pre-selected specialty.

The queried codes can be queried for a pre-selected query time period (e.g. 1 month, 1 year, 2 years, 5 years, etc.). Records having the queried codes can be further queried to account for a particular care provider (e.g. identifier associated with the care provider, care provider's name, etc.) and text within the record(s) can also be queried for data related to success measures, complication measures, or other information.

The querying that is performed can also be configured to account for specialties that may require a team of care provider personnel. For instance, there can be care provider surgical teams for some complex surgical procedures in which a common surgical team is regularly used for a care provider to provide such a service. The querying that is performed can evaluate the entire surgical team as a care provider entity instead of a single care provider surgeon, doctor, dentist, or other type of care provider. Examples of such specialties that may involve a team based evaluation can include:

a. Separation of Siamese twins (team of neurosurgeons and/or orthopedic surgeons)
b. Esophageal cancers (team of general surgeons and/or thoracic surgeons)
c. Pituitary tumors (team of otolaryngology surgeon, neurosurgeon); and
d. Sinus cancers invading the brain (team of head and neck cranial base surgeon, oculoplastic surgeon and cranial base neurosurgeon, and an electrophysiologist for intraoperative neurophysiologic monitoring).

The querying performed for a particular set of teams can be obtained based on team identification (e.g. names of team members, a pre-defined self-reported code for the team, etc.). The querying can be performed to corroborate self-reported data concerning the volume of work in a particular specialty requiring use of the team, success rates for the team and complication rates for the team. The querying and evaluations performed by a host device 5 for a particular team can utilize the exemplary querying and evaluation processed described below or elsewhere herein.

The medical records identified via the querying can then be stored at the host device 5 for subsequent comparison with the self-reported data received from the care provider via that care provider's care provider device 7 to evaluate success measures and complication measures. Alternatively, the host device 5 can communicate with the EHR device 9 and/or practice management element PM having the queried medical records and/or billing records to perform the comparison. The comparison can include querying the medical record data and/or billing record data obtained via the EHR device and/or practice management element PM for pre-defined success measure data (e.g. text) that is associated with at least one success measure and pre-defined complication measure data (e.g. text) that is associated with at least one complication measure. Complication and success rates for the queried medical record data can then be calculated based on the queried results.

For example, a complication rate for a provider can be calculated by the host device 5 utilizing a complication rate calculation that defines the complication rate as being a number of identified complications determined from the overall number of applicable records (e.g. [identified complications for a specialty]/[overall number of medical records for that specialty that were queried]×100=% complications, or a complication rate). As another example, a success rate for a provider can be calculated by the host device 5 utilizing a success rate calculation that defines the success rate as being a number of identified successes determined from the overall number of applicable records (e.g. [identified successes for a specialty]/[overall number of medical records for that specialty that were queried]×100=% success or a success rate).

The host device 5 can compare the queried and analyzed medical record data obtained via the one or more EHR devices 9 and/or practice management elements PM with care provider self-reported data received by the host device 5 via a care provider device 7. The comparison that is performed can include comparing the self-reported success rates and complication rates with the success and complication rates the host device 5 determined from the queried electronic record data. The host device 5 can be configured to determine the self-reported data is corroborated and reliable in the event the self-reported data is within a pre-selected threshold value of the calculated values. For instance, the self-reported success measure data of the care provider can be considered corroborated and reliable in the event the host device 5 success rate evaluation of the queried electronic medical record data obtained via one or more EHR devices 9 and/or practice management elements PM is greater than or equal to the success rate provided by the care provider. As another example, the self-reported complication measure data of the care provider can be considered corroborated and reliable by the host device 5 in the event the host device 5 complication rate evaluation of the queried electronic medical record data obtained via one or more EHR devices 9 and/or practice management elements PM is less than or equal to the self-reported complication rate provided by the care provider via the care provider device 7.

Other self-reported data in addition to success measures and/or complication measures can be compared and corroborated as well. For instance, self-reported specialization experience data or other data can also be corroborated by the host device 5 communicating with one or more EHR devices 9 and/or practice management elements PM to evaluate medical records and billing records involving the care provider for a particular pre-defined specialty.

For example, the host device 5 can communicate with one or more EHR devices 9 and/or practice management elements PM to obtain copies of records involving a care provider to query those records or can communicate with the EHR device(s) 9 and/or practice management elements PM to query the records maintained by those devices for a particular specialty. Such queries can include a query by a particular code. For example, the host device 5 can perform a query of records that queries a care provider identifier (e.g. name, code associated with the care provider to identify that care provider) along with a pre-selected procedure code of area of expertise code associated with a specialty (e.g. one or more CPT codes, at least one ICD-10 code and/or at least one ICD-9 code defined as being associated with the specialty). The records obtained via the query can be further evaluated by the host device 5 to identify a volume of work within a pre-selected time period (e.g. number of procedures of a particular ICD-10 code or number of records showing experience with a particular IDC-9 code condition within a year). If this volume of work is at or exceeds a pre-selected threshold experience level for meeting a specialty criteria, the host device can corroborate the self-reported specialty area for the care provider. Otherwise, that self-reported data may be disregarded and not included in displays or can be flagged for further follow up to indicate the self-reported data is not accurate. The success and complication measures (e.g. success rate and complication rate) can also be evaluated via the same queried records by the host device so that the success and complication measures for that care provider's self-reported specialty can be corroborated and/or also used in other evaluations for the care provider to be performed by the host device 5.

In some embodiments, a care provider may not provide any self-reported data to a host device 5 or may only provide a limited amount of self-reported data. In such situations, the host device can be configured to generate corroborated specialty data for a care provider and/or other metrics related to the skill, experience, and/or expertise of that care provider by communicating with one or more EHR devices 9 and/or one or more practice management elements PM to query medical and/or billing records concerning that care provider and the care provider's experience. The querying can include use of a care provider name or code associated with the care provider along with other querying information as noted above (e.g. one or more CPT codes, at least one ICD-10 code and/or at least one ICD-9 code defined as being associated with the specialty that may be within a pre-selected time period and/or text searching of related records (e.g. surgical notes, etc. as noted herein) for evaluation of complication rates and success rates for the care provider). Such queried information can be utilized to form corroborated data for the care provider related to various experience, skill and/or expertise the care provider may have. This type of generated corroborated data can also be considered validated data and/or authenticated data. This type of corroborated data can be utilized to compare the care provider to other care providers of a database accessible to the host device 5 for generation of a quality rating or other type of evaluation indicia for the care provider that can compare the care provider to other care providers in a database or data store accessible to the host device 5 (e.g. a star rating or other type of rating as discussed herein, etc.).

The host device 5 can also be configured to utilize the corroborated data to facilitate GUI displays at patient devices to provide improved communication of care provider qualifications, skills, and experience to users. This can help improve the user's ability to select a care provider for further communicating with via the host device 5 and provide a more efficient, improved communication processing for users and care provider communicative engagement for arranging health care services for different users. For example, the host device 5 can be configured to analyze a cohort of corroborated care provider data stored in at least one data store 13b of the memory 13 accessible to the host device 5 (e.g. memory of the host device 5 or memory of a database server that is accessible to the host device via a network connection or other type of communicative connection). The analysis performed by the host device can filter care providers for rating care providers for a pre-selected procedure, medical condition, or specialty area. The cohort data can include host device corroborated determinations on care provider complication measures, success measures, and volume (e.g. number of procedures within a pre-selected time period). The care providers having the highest success measure(s) and lowest complication measures can be filtered so they are rated more highly than care providers with lower success measures and/or higher complication measures. The volume of procedures can be utilized in the filtering so a care provider with a number of procedures below a pre-selected volume is omitted from the searched results via the filtering and so that a care provider with a higher volume and similar success and complication measures is rated above a care provider with a lower volume.

Success measures utilized by the host device 5 can include utilization of pre-operative and post-operative questionnaire records concerning patient reported outcome measures (PROMs) (e.g. PROM records). Identified improvements from PROM record evaluations can be used to indicate success and identified decreases (e.g. non-improvement, declined condition, etc.) from the PROM record evaluation can be utilized to indicate a lack of success. For example in orthopedic surgery, these questionnaires determine the status of pain, mobility and quality of life measures. The improvement or degradation of post-op questionnaires compared to pre-op can be utilized for a determination of quality.

The host device 5 can also utilize querying and/or obtained record evaluation to detect care providers who may be determined to have a low quality or an unacceptable error in the care provider's history for either identifying such an issue to a user or removing the care providers from consideration so that the care provider having such a past problem is never even identifiable to a user. For instance, the host device 5 can be configured to determine whether a care provider ever performed a procedure on the wrong side of a patient or at a wrong site of a patient (e.g. replaced a patient's left knee instead of the patient's right knee, performed a procured on patient A when the procedure should have been performed on patient B, etc.).

Figure 9:
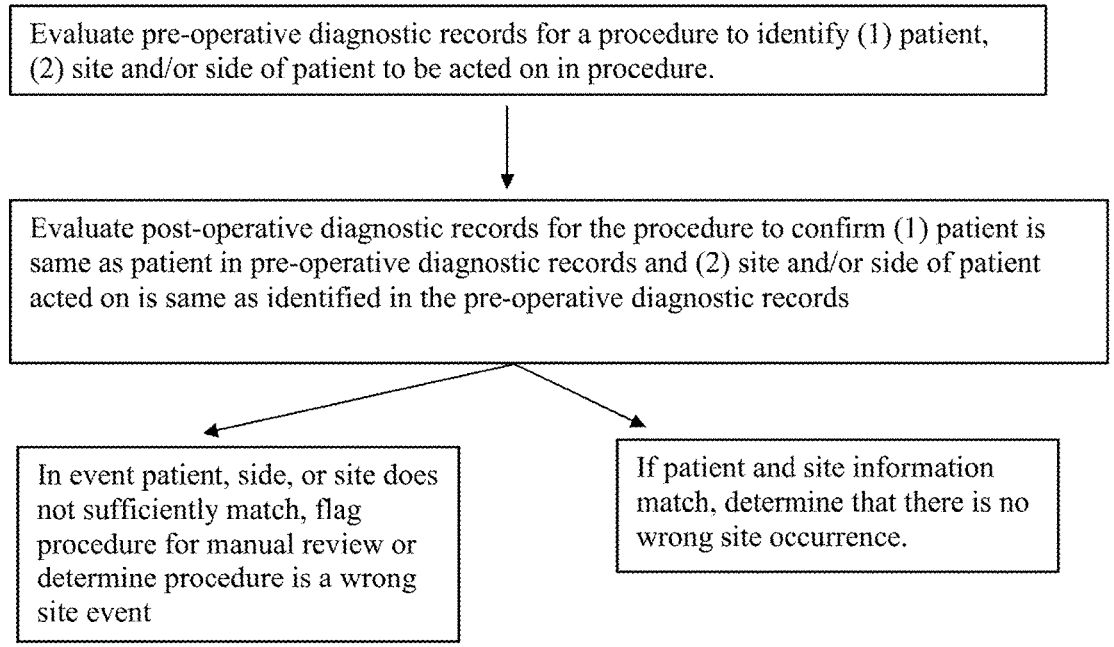
FIG. 9 is a flow chart illustrating an exemplary wrong site evaluation process that can be utilized by the first exemplary embodiment of the telecommunication apparatus.

An example of a low quality or unacceptable error evaluation process is shown in FIG. 9. For instance, the host device 5 can perform a comparison of pre-operative records and post-operative records to confirm that procedures to be performed on a right or left side of a patient were in fact performed on that right or left side. One example of such a comparison is to dismiss the processing if pre-operative records (e.g. pre-operative notes) indicate a procedure is bilateral and perform the processing if the pre-operative records indicate a procedure is to be performed on a left side or right side. In the event a pre-operative record shows a procedure is to be performed on a left side, the post-operative records (e.g. post-operative notes or post-operative diagnosis) can be evaluated to verify that the left side is properly indicated. If the left side is not indicated, the event can be flagged for subsequent manual review of the event for subsequent entry via manual input on whether a wrong side or wrong site event occurred for that procedure for storage and use by the host device 5. Or the host device 5 can be configured to automatically determine that the procedure was performed on the wrong side based on the performed evaluation.

The wrong site evaluation process can also be performed to account for other wrong-site errors. For instance, the host device 5 can perform a comparison of pre-operative records and post-operative records to confirm that procedures to be performed on particular site of a patient were in fact performed on that site. One example of such a comparison is to evaluate the pre-operative records (e.g. pre-operative notes) to identify at least one site on which a procedure is to be performed (e.g. L1-L2 disc herniation, right knee, left elbow, chest, etc.) and then evaluate the post-operative records (e.g. post-operative notes or post-operative diagnosis) to verify that the identified site(s) were acted upon (e.g. are properly indicated). If the identified sites to be worked on from the pre-operative record evaluation is not indicated, the event can be flagged for subsequent manual review of the event for subsequent entry via manual input on whether a wrong site event occurred for that procedure for storage and use by the host device 5. Or the host device 5 can be configured to automatically determine that the procedure was performed on the wrong site based on the performed evaluation.

The wrong site evaluation process can also be performed to account for other wrong-site errors. For instance, the wrong site evaluation process can be performed to also indicate a wrong site occurrence occurred due to operation on the wrong patient. For example, the host device 5 can perform a comparison of pre-operative records and post-operative records to confirm that procedures to be performed on a particular patient were in fact performed on that patient. Such an evaluation can occur at the same time the evaluation of whether the correct site and/or correct side of a patient was acted on as noted above. For wrong patient evaluations, the host device 5 can evaluate the pre-operative records (e.g. pre-operative notes) to identify the patient on which a procedure is to be performed and then evaluate the post-operative records (e.g. post-operative notes or post-operative diagnosis) to verify that the identified patient was actually the patient who received that procedure (e.g. the patient name is consistent or the same for the pre-operative and post-operative records). If the identified patient identified from the pre-operative record evaluation is not indicated in the post-operative records, the event can be flagged for subsequent manual review of the event for subsequent entry via manual input on whether a wrong site event occurred (e.g. procedure performed on wrong patient) for that procedure for storage and use by the host device 5. Or the host device 5 can be configured to automatically determine that the procedure was performed on the wrong site (e.g. wrong patient) based on the performed evaluation.

In some embodiments, the evaluation of care provider records (e.g. pre-care providing records, pre-operative notes, operative notes etc.) can include comparing the term frequency included in the operative notes records. The term frequency evaluation can focus on one or more pre-selected keywords defined for a particular type of procedure. For instance, for operative notes for a knee replacement procedure the term "knee" and/or the term "popliteal artery" can be at least one pre-selected keyword term. A care provider's operative note records for the same care providing procedure (e.g. the same type of surgery) can be evaluated to identify a threshold keyword value (e.g. an average number of times at least one pre-selected keyword appears in the operative notes, a median value for the number of times at least one of the pre-selected keyword terms appears in the operative notes, a value that is a pre-selected amount greater than the median number of times the at least one term appears in the operative notes—e.g. a value that is 10% or 20% greater than a median value for the number of times the term appears in the operative notes of the care provider for that type of procedure). Alternatively, such a keyword threshold value can be a defined specific number of times a term could appear in the operative notes. The evaluation that is performed can be for each keyword (e.g. the threshold to be reached can be at least the threshold number of instances for the term "popliteal artery"). In other configurations, the evaluation that is performed can be for a threshold number of instances for a phrase or a group of terms that are within a pre-defined close proximity to each other (e.g. at least a number of pre-selected instances of the term "popliteal artery" appearing within 5 word of the term "blood,", "bleeding", "bleed", "aneurysm", or "hemorrhage".).

The host device 5 can be configured to perform an evaluation of a care provider's quality at performing a type of service or procedure (e.g. a knee surgery, etc.) by evaluating the number of times a pre-selected keyword term (e.g. "knee") on average is found in the operative notes for all the care provider's services of procedures for that type of service or procedure (e.g. knee surgeries performed within a pre-defined time period) can be used as the keyword threshold value, for example. An evaluation of such records to identify a median value can be used as an alternative example for the keyword threshold value.

The host device 5 can be configured so that each of the operative notes for the care provider for the type of service for all that provider's patients for a procedure type that include instances of one or more keywords that exceed the defined keyword threshold value can be flagged for manual review for possible negative outcomes that can affect a quality rating. Manual review can then result in providing input to the host device 5 for indicating a negative indication or not for each flagged record. Or, each of the operative notes for the care provider for all that provider's patients that have instances of at least one keyword that exceed the keyword threshold value can be determined to be a care providing procedure having a negative outcome indicator by the host device 5 for use in rating of the care provider.

The host device 5 can also, or alternatively be configured to evaluate pre-care providing records (e.g. pre-operative notes and other pre-operative records for a procedure to be performed on a de-identified patient) with related post-care providing records (e.g. post-operative notes or other post-operative records for a particular procedure to be performed as indicated by the pre-operative records for the procedure performed on the de-identified patient). This type of evaluation can include a comparison between the pre-care and post-care related records that can include one more keyword searches.

For instance, the host device 5 can be configured to utilize one or more natural language processing (NLP) algorithms to perform keyword searches and comparisons. For instance, the host device 5 can perform a search for one or more keywords of unexpected symptoms in post-operative care providing records (e.g. post-operative office visit notes or post-operative surgery records, etc.). For example, the host device can evaluate a care provider's post-operative care providing records for a hernia surgery to find terms that are pre-defined as being associated with a patient experiencing abdominal pain that is unrelenting and/or related post-operative records showing a negative result from that surgery (e.g. CT scan showing air in the abdominal cavity caused by perforated bowel that occurred during the hernia surgery).

As another option, which can be done in combination with or as an alternative to the above noted examples, the host device 5 can utilize a pre-defined NLP algorithm for evaluation of keywords of patients being referred to other surgeons in other specialties that can be identified in post-care providing documents (e.g. noted in post-operative office visit note documents). For example, a search for referrals to other care providers in post-operative notes can be performed to identify situations where the care provider's care resulted in a patient having a new health issue and, instead, has to refer the patient to another care provider to resolve or care for that new health issue (e.g. a patient is referred to an ear note and throat (ENT) surgeon who finds a vocal cord paralysis from recurrent laryngeal nerve injury that occurred during the patient's first surgery with the referring surgeon). The host device 5 can also be configured to also evaluate referred care provider records identified from the keyword searching to identify a negative quality event or to flag such an event for further manual review. The referred care provider records can be included in the referring care provider's records that are obtained by the host device 5 for evaluation of those documents.

For instance, the host device 5 can be configured to identify the referred care provider identified in documents and perform a search of the care provider's records to evaluate the records related to the referred surgery for evaluation of whether a negative care event occurred (e.g. surgical injury to a patient identified by the referred care provider, etc.). Such record evaluation can include a combination of keywords and de-identified patient record information for cross-references the relevant records for performing the keyword searching to evaluate the referred care providers records for identification of a negative care providing occurrence.

As another option, which can be done in combination with or as an alternative to the above noted examples, the host device 5 can be configured to perform a pre-defined NLP algorithm evaluation for searching for keywords within post-operative care records for a care provider in which that care provider referred patients to other surgeons in the same specialty based on keywords and names identified in the post-operative care records (e.g. post-operative office visit notes). Identification of such referrals can indicate patients are being referred to other surgeons with more experience to complete a procedure or provide care because the referring care provider is not qualified enough or skilled enough to provide that care. Such findings can be considered a negative quality of care indicator for use in care provider evaluations and ranking of care providers.

The negative quality indicators identified from the keyword searching can be considered a complication measure, a type of complication measure, or other negative quality indicator measure. Such indicators can be used in conjunction with other indicators identified from the host device's evaluation of care provider related documents obtained from care providers devices 7 and EHR devices 9 to determine an overall quality indication for the care provider for a particular type of procedure (e.g. a particular type of surgery, a particular type of care providing service, etc.).

The host device 5 can utilize a pre-selected weighing criteria to weigh multiple success measures, complication measures and the volume for a particular category for filtering the care provider data and generating quality indicia for the highest rated care providers identified from the filtering. For example, some complication measures can be weighed to be more significant than others while other some success measures can be weighed to be more significant than others. A weighing factor for volume can also be defined for the host device to weigh the various factors when filtering the care provider data to provide a ranked listing of care providers so that the care providers determined to have the highest quality rating via the weighed factors are shown as the top results from the filtering. The weighing factor can also be determined so that a care provider found to have had a wrong site error (e.g. wrong site error, wrong patient error, wrong side error) is determined to have a lowest rating or be assigned a non-use rating to remove the care provider from any type of consideration or display as an option to a user.

The host device 5 can also determine a quality indicator, such as a star rating, a numerical rating, or other rating indicia for display with the filtered list so that the filtered result data is communicable to a patient device via a network connection (e.g. an API interface communicatively connecting the host device 5 to a patient device 1 via at least one network) for display on a patient device's displayed GUI for illustrating the filtered results along with the quality indicia identifying the determined quality metric for identified care providers. FIG. 8 illustrates an example of such a GUI that can be generated in response to filtering input that identified a colonoscopy procedure as a surgical procedure of interest to a user.

The host device 5 can be configured to receive filtering input from a patient device to generate a display of care provider data via a GUI displayed at the patient device based on the filtering input that was received. The filtration function performed by the host device 5 can be configured to filter the care provider data based on a number of different filtering options. Example filtering options include one or more of:
 a. Out-of-pockets costs;
 b. Proximity to site of service;
 c. Volume of cases;
 d. Success Measures;
 e. Complication Measures; and
 f. Opinions (alternatives to surgery etc.).

The host device 5 can have an application 13*a* stored in its memory that includes search engine function or includes a search engine application to facilitate the filtering of the data based on the filtering input received from a patient device 1. The options for GUI display of filtered data results can include a display of care providers in accordance with a pre-selected priority of appearance criteria. An example of a filtered data priority of appearance criteria can include:
 1. Care providers who feel surgery is not necessary;
 2. Care providers who recommend alternatives to surgery;
 3. Care providers who recommend an alternative approach to surgery, minimally invasive. Example is functional endoscopic sinus surgery (performed in an ASC with 3-5 day recovery) and minimally invasive balloon sinuplasty (performed in an office setting with 24 hour recovery);
 4. Care providers who recommend an entirely different approach to surgery; and
 5. Care providers who recommend surgery having the highest quality rating determined based on a pre-selected weighing function that factors volume, success measures, and complication measures.

In some embodiments, the generation of the GUI can be configured to provide different tiers of care providers. A first tier (e.g. a top tier or a non-surgery indicated tier) can be presented to provide the user with a visual list or other indicia of care providers would do not believe a particular condition for the user requires surgery or who empirically has such a viewpoint based on the care provider's past records evaluated by the host system. A second tier or middle tier of care providers can also be shown on the GUI. This second tier or middle tier can include care provides who empirically utilize conservative alternative options to surgery (e.g. non-surgical treatment or minimally invasive approaches). This second tier or middle tier can include a list of ranked care providers who have responded to a user's initial request for care or can be selected based on empirical history of the care provider's work performed by the host device 5. A third tier or bottom tier of care providers can also be presented to the user via the GUI. This third tier or bottom tier can include a list of ranked care providers who have responded to a user's initial request for care or can be selected based on empirical history of the care provider's work performed by the host device 5.

Embodiments of the filtering can be configured so that an identification of care providers who recommend an alternative approach to surgery that is minimally invasive (e.g. recommends against a functional endoscopic sinus surgery having a 3-5 day recovery in favor of a minimally invasive balloon sinuplasty that can be performed in an office setting with 24 hour recovery). The host device 5 can include a data store 13b that is structured as a database of procedures for minimally invasive alternatives to different surgeries that can be utilized in the filtering and prioritization of GUI display. The database can be utilized to identify suitable care providers who recommend a pre-selected alternative surgery based on the filtering input to illustrate in accordance with the pre-selected optimization scheme, for example.

Figure 6:
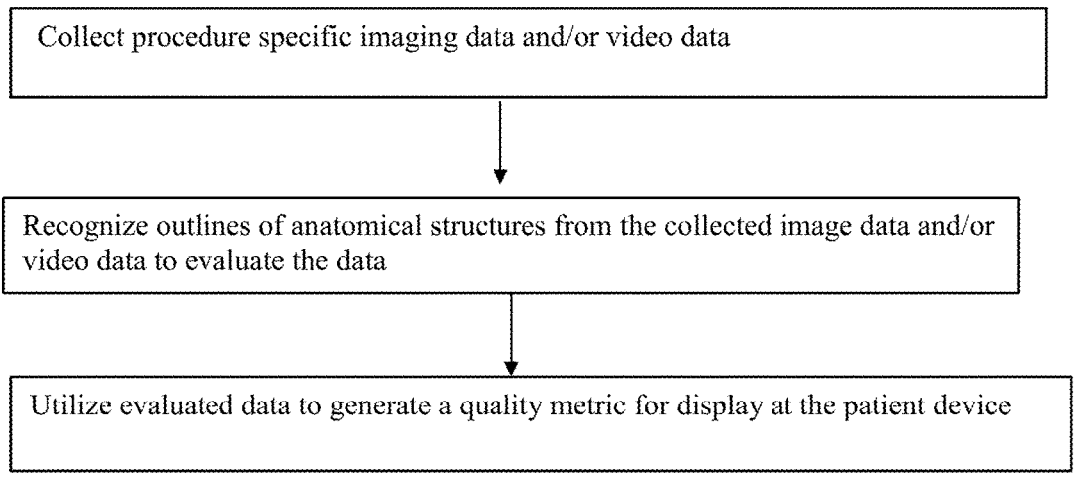
FIG. 6 is a flow chart illustrating an exemplary process for generating a quality metric for display in a GUI of a patient device 1 in the first exemplary embodiment of the telecommunication apparatus.
Figure 7:
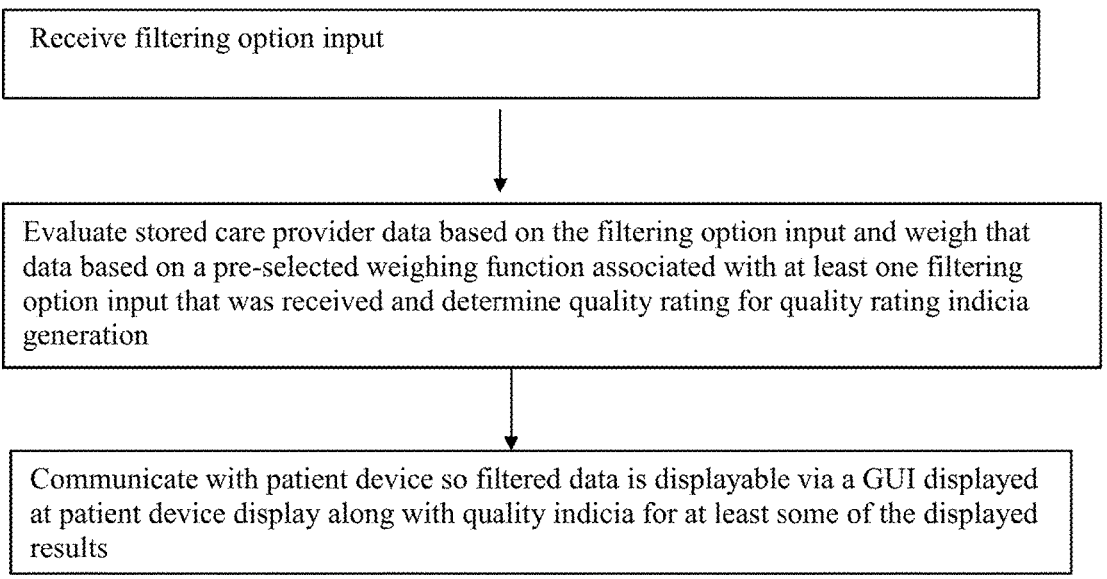
FIG. 7 is a flow chart illustrating an exemplary process for filtering care provider data for display on a GUI at a patient device, which can be supported by the host device 5 in the first exemplary embodiment of the telecommunication apparatus.

As may best be appreciated from FIG. 6, corroboration of care provider data can also be configured at the host device 5 to take into account image sensing technology and machine learning for evaluation of surgeons for a pre-selected set of surgical procedures so that critical view of safety (CVS) for different care providers for those surgical procedures can be evaluated and corroborated. CVS can be utilized as a quality indicator for being weighed in conjunction with filtering input so that a quality indicator shown to a user via the patient device GUI incorporates CVS related data as well as other factors.

In one exemplary CVS quality determination and corroboration process, procedure specific imaging data and/or video data for a surgical procedure can be collected from a care provided for one or more procedures the care provider performed. The host device 5 can receive that data for storage in memory of the host device 5 and/or memory accessible to the host device 5. The image data and/or video data can then be analyzed and evaluated to recognize outlines of anatomic structures associated with the surgical procedure based on surgical procedure description data provided by the care provider that is associated with the collected image data and/or video data. The host device 5 can communicate the image and/or video data to one or more other surgeons at their care provider devices for review and validation of the image results to corroborate the procedure was performed consistent with CVS for that particular procedure (e.g. the procedure was stopped before a particular anatomical structure was inadvertently injured or otherwise affected). The host device 5 can be configured to employ a machine learning algorithm to facilitate surgeon feedback on that data to help supplement that feedback data for development of the CVS rating. The CVS rating can then be included in the quality indicia factors for weight and use in determining a quality indicator. The CVS rating can also be displayed and/or provided independent of the overall quality rating determined for a particular care provider's expertise in connection with a particular procedure or specialty.

The host device 5 can be configured to transfer data between the host device 5 and the care provider devices 7 and also transfer data between the patient device 1 and one or more care provider devices 7 to help protect privacy and help improve the safety and privacy of the communicated data. In some embodiments, the host device can require the patient device 1 to provide a public key associated with patient records. The public key can be transmitted to require the host device to utilize a private key to unlock and obtain access to the patient documents associated with the public key. A block chain scheme can be utilized for this exchange of public keys and use of private keys in some embodiments.

The host device can also send a public key related to access to patient documents or files to one or more care provider devices 7 so the care providers are required to submit the public key to access those documents. The public key can be transmitted to require the care provider device to utilize a private key to unlock and obtain access to the patient documents associated with the public key. A block chain scheme can be utilized for this exchange of public keys and use of private keys in some embodiments.

In some embodiments, the host device 5 can send public keys to care provider devices for the care provider device to utilize to access de-identified data of a medical record. The private key can be needed to unlock and visualize such data at the care provider device. The host device 5 can also require at least one public key from a patient device 1 for use in accessing de-identified data of at least one medical record of a patient associated with that public key. The private key can be needed to unlock and visualize such data at the host device 5.

The host device 5 can be configured to maintain one or more private keys or provide private keys to the patient device in some embodiments. Access to a private key may be provided by the host device 5 after a care provider device 7 authenticates its ability to obtain access to the private key. The host device 5 can also be configured to request and obtain a private key from an EHR device 9, practice management element PM, or other authorized access providing device that may manage private keys associated with patient record public keys for patient medical record related documents or files.

The host device 5 can be configured to utilize de-identified records retrieved from care provider devices 7 or at least one EHR device 9 to perform evaluations of that data, store that data, or otherwise use that data as discussed herein.

Figure 10:
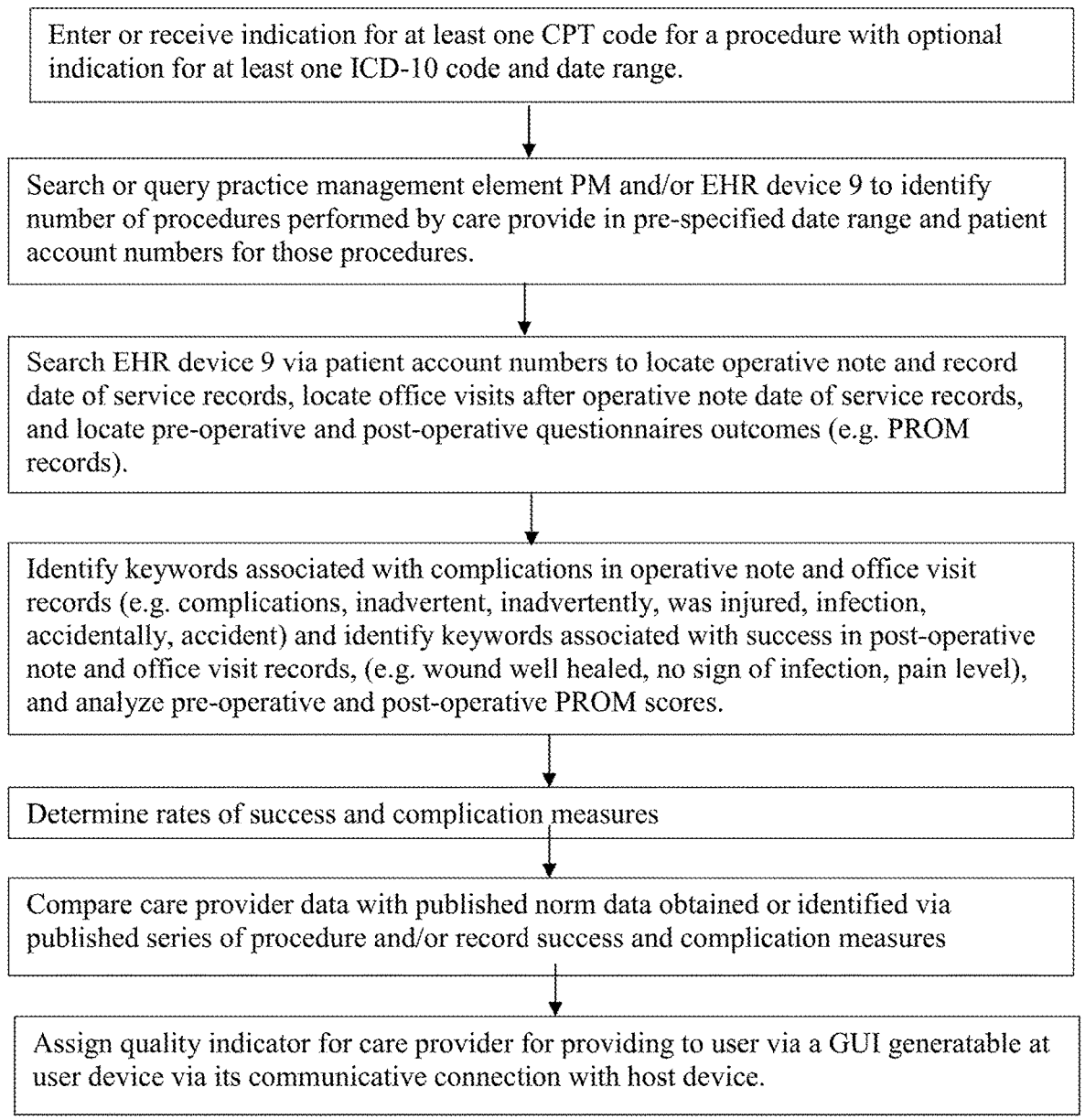
FIG. 10 is a flow chart illustrating an exemplary embodiment of a querying an evaluation process for generating a quality metric for display in a GUI of a patient device 1 that can be utilized by the first exemplary embodiment of the telecommunication apparatus.

As can be appreciated from the above, embodiments can be configured to query various medical and/or billing records to facilitate the evaluation of care provider skill and prior experience for displaying indications to a user about the quality or skill of one or more care providers that is based on an evaluation of past empirical data. FIG. 10 illustrates another exemplary methodology, or process, that can be utilized by an embodiment of the apparatus to facilitate such functionality.

Referring to FIG. 10, an embodiment can be configured to receive input indicating at least one CPT code for a procedure. A date range and/or an ICD code can also be provided as input. In other embodiments, the date range or ICD code may not be utilized and only the input concerning the CPT code may be utilized. Examples of input that can be provided can be a user using a user device to provide data to the host device via a communicative connection between the user device 1 and the host device 5 that provides data that can be associated within at least one CPT code. Such data can include the user providing a CPT code, utilizing a GUI to provide input to identify at least one CPT code, or entering text that can be associated with at least one CPT code, for example.

After receiving the input data, the host device 5 can be configured to search records from one or more EHR devices 9 and/or one or more practice management elements PM to identify the number of times a procedure was billed for a care provider within a pre-defined data range (e.g. a pre-selected date range, a date range defined by user input, etc.). These records can also be searched to list the patient account numbers associated with those past procedures.

The searching of the patient account number and procedure data can be performed by the host device 5 searching records it previously obtained from one or more EHR devices 9 and/or one or more practice management elements PM via prior querying and/or communications. It can also, or alternatively, include the host device 5 querying one or more EHR devices 9, at least one care provider device 7 and/or one or more practice management elements PM to search to identify the procedure history in which a care provider billed for the identified procedure and obtain the patient account numbers associated with such procedures.

The host device 5 can utilize the patient account numbers that are identified and/or obtained to subsequently perform querying of other medical records and/or records available via one or more EHR devices 9 to (a) locate operative note and record date or service for the different procedures performed by the care provider, (b) locate or identify office visit and operative note date of service information, and (c) locate or identify pre-operative and post-operative questionnaire records concerning patient reported outcome measures (PROMs) (e.g. PROM records).

The host device 5 can then search the located and/or identified documents (e.g. operative note documents, PROM records, etc.). This searching can include (a) identifying pre-defined keywords associated with complications in operative note and office visit records (e.g. complications, inadvertent, inadvertently, was injured, infection, accidentally, accident, outcome measures, etc.), (b) identify pre-defined keywords associated with success in operative note and office visit records (e.g. wound well healed, no sign of infection, pain level, etc.), and (c) analyze the pre-operative and post-operative questionnaire records (e.g. evaluate pre-operative and post-operative PROM scores, etc.).

The host device 5 can also extract documents or records having relevant data that was identified and de-identify those documents or records. Those records or data obtained from those records can be used by the host device to calculate rates of success and rates of complication measures (e.g. use of the above noted exemplary processes for such calculations). The records can also be analyzed to the improvement or decline in PROMs (e.g. improvement or decline in PROM scores based on differences in the pre-operative and post-operative questionnaire records, etc.). Such a measure can be factored into the successful or complication outcomes or can be a separate parameter utilized to identify an average or median PROM score change for the procedures involving the CPT code for the care provider. The evaluated documents can also include additional keyword searching and document evaluation as discussed above for procedures performed by the care provider (e.g. evaluation for referrals, evaluation for identification of complications or problems caused from a procedure performed by the care provider, evaluation of post-operative and pre-operative documents to identify a failure to resolve a problem or creation of a new symptom or problem for the patient, etc.).

The host device 5 can identify retrospective published series of procedure and record success and complication measures and compare those results with the data obtained about the care provider's past history with the procedure. This comparison can be utilized in conjunction with assignment of a quality indicator, such as a star rating, a numerical rating, or other rating indicia a grade (e.g. as indicated in FIG. 8 and discussed above). The host device 5 can communicate with a user device 1 so that the determined quality indicator can be presented to a user via a GUI (e.g. as shown in the example of FIG. 8).

For the exemplary process shown in FIG. 10, it should be appreciated that the evaluation can be configured in some embodiments to only utilize the corroborated data corroborated via the above discussed corroboration processing. In other embodiments, the process can utilize (or can also utilize) non-corroborated data (e.g. data that is non-corroborated meets a pre-selected reliability threshold). Also, care providers identified as having too low a rating or as having a wrong side/wrong patient/wrong site type error from the performed evaluation may be removed from consideration or otherwise be identified so that a GUI shown to the user does not identify such a care provider as discussed above.

The host device 5 can perform this processing for all relevant care providers in a database or other data store that is associated with the user input identified CPT code for a particular procedure so that the use can be presented with the quality indicators for numerous care providers at the same time as shown in the example of FIG. 8 for example.

The host device 5 can also be configured to communicate with at least one EHR device 9 and/or at least one care provider device 7 to facilitate use of a service hosted by the host device 5. For example, a care provider can utilize a care provider device 7 to communicate with the host device 5 to identify a patient who is a user of the service offered by the host device 5 and send an electronic message (e.g. email message, text message, etc.) to a user device of the patient that indicates a care provider may be needed to be evaluated or selected for providing a health care service (e.g. a surgery) to the patient. The message and include a link or other information to help the patient utilize the service offered by the host device to review potential care providers and select a suitable care provider option via the user device 1 of the patient communicating with the host device 5. For example, the link can be actuated by the patient using the user device and that can result in a GUI being displayed to the user that identifies care providers in his or her area that may be suitable options for providing the health care service. The GUI that is displayed can include an exemplary GUI such as, for example, the exemplary GUI shown in FIG. 8 or other similar type display. The GUI can alternatively be a home screen type display that allows a user to enter data to provide filtering of care provider data to result in a subsequent display similar to the exemplary display of FIG. 8 or other suitable type of display that can identify care provider options that include a quality indicator or quality indicator indicia for the different options.

Embodiments of the telecommunication apparatus, device, and method can be designed to help avoid a situation where a medical care provider's input data misrepresents the level of expertise, skill, or experience of the care provider. This can help improve communications for obtaining health care services, and help avoid situations where a care provider is selected by a patient for a service without the patient having a complete understanding of the care provider's level of skill or applicable experience for the services needed by the patient. The improved communications provided by embodiments of the apparatus and method can provide increased awareness to a prospective patient of the care provider options available to the patient so a more accurate selection of a suitable care provider can be made by the patient. This can also have other benefits. For instance, such features can help reduce incidents of malpractice, and help lower insurance premiums for care providers and patients as more suitable care providers can be more easily identified and selected by prospective patients.

It should be understood that different embodiments can be developed to meet different sets of design criteria. For example, the particular type of network connection, server configuration or client configuration for a device for use in embodiments of the method or telecommunication apparatus can be adapted to account for different sets of design criteria. As yet another example, it is contemplated that a particular feature described, either individually or as part of an embodiment, can be combined with other individually described features, or parts of other embodiments. The elements and acts of the various embodiments described herein can therefore be combined to provide further embodiments. Thus, while certain exemplary embodiments of a telecommunication apparatus, telecommunication device, terminal device, a network, a server, a communication system, a non-transitory computer readable medium, and methods of making and using the same have been shown and described above, it is to be distinctly understood that the invention is not limited thereto but may be otherwise variously embodied and practiced within the scope of the following claims.

What is claimed is:

1. A telecommunication apparatus comprising:
   a host device having a processor connectable to a non-transitory computer readable medium, the host device configured to communicate with at least one electronic health record (EHR) device, at least one practice management element, at least one care provider device, and at least one patient device via at least one network;
   the host device configured to query electronic medical records stored at least one of the EHR device and the at least one practice management element and compare self-reported data associated with a care provider received via the at least one care provider device with medical records associated with the care provider accessible via the at least one of the EHR device and the at least one practice management element;
   wherein the host device is configured to evaluate at least one success measure based on a pre-selected success criteria and at least one complication measure based on pre-selected complication criteria from comparing the self-reported data with data from the queried medical records to corroborate the self-reported data via evaluation of pre-operative diagnostic records and post-operative diagnostic records of the medical records to identify events in which a side or site of a patient identified in the pre-operative diagnostic records does not match a side or site of the patient identified in the post-operative diagnostic records to determine a rate of complication measure for the care provider.

2. The telecommunication apparatus of claim 1, wherein the host device is also configured to evaluate the at least one success measure based on the pre-selected success criteria and the at least one complication measure based on the pre-selected complication criteria from comparing the self-reported data with data from the queried medical records to corroborate the self-reported data via identifying keywords associated with complications in operative notes of at least one of the medical records and office visit records of the medical records to determine the rate of complication measure for the care provider.

3. The telecommunication apparatus of claim 2, wherein the host device is configured to filter the corroborated self-reported data based on filtering input received via the at least one patient device to display care provider data responsive to the filtering input.

4. The telecommunication apparatus of claim 3, wherein the filtered corroborated self-reported data is prioritizable based on a pre-selected prioritization weighing function so that care provider data is displayable via a graphical use interface (GUI) displayed at the at least one patient device in accordance with a ranking defined by the weighing function that is determined by the host device.

5. The telecommunication apparatus of claim 2, wherein the pre-selected success criteria includes a generated quality metric for a critical view of safety (CVS) criteria, the quality metric for CVS being determinable by the host device via a recognition of anatomical structure outlines from at least one of image data and video data received from the at least one patient device associated with a care provider.

6. The telecommunication apparatus of claim 1, including at least one of: the at least one patient device, the at least one care provider device, the at least one practice management element, the at least one EHR device, and the at least one network.

7. A method of telecommunication, comprising:
   a host device communicating with at least one of: at least one electronic health record (EHR) device and at least one practice management element to query electronic medical records stored at the at least one of the EHR device and the at least one practice management element, the host device having a processor connected to a non-transitory computer readable medium;
   the host device comparing self-reported data associated with a care provider received via at least one care provider device with medical records associated with the care provider accessible via the communicating with the EHR device and the at least one practice management element, wherein the comparing of the self-reported data associated with the care provider received via the at least one care provider device with medical records associated with the care provider includes evaluating pre-operative diagnostic records and post-operative diagnostic records of the medical records to identify events in which a side or site of a patient identified in the pre-operative diagnostic records does not match a side or site of the patient identified in the post-operative diagnostic records to determine a complication rate for at least one complication measure for the care provider.

8. The method of claim 7, comprising:
   the host device evaluating at least one success measure based on at least one of a pre-selected success criteria and the at least one complication measure based on pre-selected complication criteria from comparing the self-reported data with data from the queried medical records to corroborate the self-reported data via identifying keywords associated with complications in at least one of operative notes of the medical records and office visit records of the medical records to determine the rate for the at least one complication measure for the care provider.

9. The method of claim 8, comprising:
   the host device filtering the corroborated self-reported data based on filtering input received from at least one patient device to display care provider data responsive to the filtering input.

10. The method of claim 9, comprising:
    the host device prioritizing the filtered corroborated self-reported data based on a pre-selected prioritization weighing function so that care provider data is displayable via a graphical user interface (GUI) displayed at the at least one patient device in accordance with a ranking defined by the weighing function that is determined by the host device.

11. The method of claim 8, wherein the pre-selected success criteria includes a generated quality metric for a critical view of safety (CVS) criteria, the quality metric for CVS being determinable by the host device via a recognition of anatomical structure outlines from at least one of image data and video data received from the at least one patient device associated with a care provider.

12. The method of claim 8, wherein the at least one success measure includes a success rate and the at least one complication measure includes the complication rate.

13. A non-transitory computer readable medium having an application stored thereon, the application defining a method that is performed by a telecommunication device that runs the application, the method comprising:
the telecommunication device communicating with at least one of at least one electronic health record (EHR) device and at least one practice management element to query electronic medical records stored at the at least one of the EHR device and the at least one practice management element;
the telecommunication device comparing self-reported data associated with a care provider received via at least one care provider device with medical records associated with the care provider accessible via the communicating with the EHR device and the at least one practice management element, wherein the comparing of the self-reported data associated with the care provider received via the at least one care provider device with medical records associated with the care provider includes evaluating pre-operative diagnostic records and post-operative diagnostic records of the medical records to identify events in which a side or site of a patient identified in the pre-operative diagnostic records does not match a side or site of the patient identified in the post-operative diagnostic records to determine a complication rate for at least one complication measure for the care provider.

14. The non-transitory computer readable medium of claim 13, wherein the method comprises:
the telecommunication device evaluating at least one success measure based on a pre-selected success criteria and the at least one complication measure based on pre-selected complication criteria from comparing the self-reported data with data from the queried medical records to corroborate the self-reported data via identifying keywords associated with complications in at least one of operative notes of the medical records and office visit records of the medical records to determine the rate for the at least one complication measure for the care provider.

15. The non-transitory computer readable medium of claim 14, wherein the method comprises:
the telecommunication device filtering the corroborated self-reported data based on filtering input received from at least one patient device to display care provider data responsive to the filtering input.

16. The non-transitory computer readable medium of claim 15, wherein the method comprises:
the telecommunication device prioritizing the filtered corroborated self-reported data based on a pre-selected prioritization weighing function so that care provider data is displayable via a graphical user interface (GUI) displayed at the at least one patient device in accordance with a ranking defined by the weighing function that is determined by the host device.

17. The non-transitory computer readable medium of claim 14, wherein the pre-selected success criteria includes a generated quality metric for a critical view of safety (CVS) criteria, the method also comprising:
the telecommunication device determining a quality metric for CVS via a recognition of anatomical structure outlines from at least one of image data and video data received from the at least one patient device associated with a care provider.

18. The non-transitory computer readable medium of claim 14, wherein the at least one success measure includes a success rate and the at least one complication measure includes the complication rate.

* * * * *